United States Patent [19]
Alexander

[11] Patent Number: 5,914,320
[45] Date of Patent: Jun. 22, 1999

[54] CO-MILLED MIXTURES COMPRISING POLYOL AND METHOD OF MAKING

[75] Inventor: Steven Robert Alexander, Hamilton County, Ohio

[73] Assignee: The Procter & Gamble Company, Cincinnati, Ohio

[21] Appl. No.: 08/684,118

[22] Filed: Jul. 19, 1996

[51] Int. Cl.$^6$ .............................. A61K 31/70; C07H 1/00
[52] U.S. Cl. ............................ 514/23; 514/53; 514/738; 536/119; 536/120; 536/124
[58] Field of Search ................................ 514/23, 53, 738; 536/120, 119, 129

[56] References Cited

U.S. PATENT DOCUMENTS

| | | | |
|---|---|---|---|
| 3,694,230 | 9/1972 | Cook | 426/518 |
| 3,920,819 | 11/1975 | Stephens et al. | 514/209 |
| 4,338,350 | 7/1982 | Chen et al. | 426/658 |
| 4,755,318 | 7/1988 | Davies et al. | 510/351 |
| 4,865,863 | 9/1989 | Prosise et al. | 426/518 |
| 5,001,150 | 3/1991 | Yap | 514/376 |
| 5,194,172 | 3/1993 | Taneri et al. | 510/145 |

FOREIGN PATENT DOCUMENTS

| | | |
|---|---|---|
| 0062565 | 3/1982 | European Pat. Off. . |
| 1079265 | 8/1967 | United Kingdom . |
| 1089523 | 11/1967 | United Kingdom . |

OTHER PUBLICATIONS

Cane Sugar Handbook, by George P. Meade, Spencer–Meade, Ninth Edition, 1963, pp. 263–266.

*Primary Examiner*—Elli Peselev
*Attorney, Agent, or Firm*—Dinsmore & Shohl

[57] ABSTRACT

A process for making a mixture of polyol and at least one additional reaction component for the manufacture of polyol fatty acid polyesters comprises co-milling the polyol and the additional reaction component. The co-milling reduces the particulate size of the polyol and the additional reaction component while creating particles which include an admixture of polyol and the additional reaction component. The co-milled mixture of polyol and additional reaction component can be used, for example, as a feed stream for the transesterfication reaction of the polyol to produce a polyol fatty acid polyester.

49 Claims, No Drawings

CO-MILLED MIXTURES COMPRISING POLYOL AND METHOD OF MAKING

TECHNICAL FIELD

This invention relates to co-milled mixtures of a polyol and one or more other reaction components employed in polyol fatty acid polyester manufacture. Additionally, this invention relates to methods of making co-milled mixtures of finely ground particles of polyol and finely ground particles of other reaction components and finely ground particles in which the polyol and other components are in admixture. The present invention is further directed to processes for making polyol fatty acid polyester, in which processes a co-milled mixture of polyol, fatty acid soap or other reaction component is employed as a feed stock for the reaction producing the polyol fatty acid polyester.

BACKGROUND OF THE INVENTION

Processes for the milling of polyols, such as sucrose, are known in the art. Milling is often desirable to reduce the size of crystalline particles of polyol, e.g., sucrose particles, and facilitate handling or storage of the polyol and/or mixing of the polyol with other components.

Processes for co-milling of polyols in the presence of additional components, e.g., starch or flour, is also known. For example, U.S. Pat. No. 3,694,230 to Cooke describes a co-milling process for making culinary mixes. Specifically, Cooke describes a process of co-milling flour and sugar together to make a primary ingredient for a cake mix. The sugar and flour are co-milled together prior to mixing with additional baking materials in order to make a more uniform mixture, resulting in easier preparation of the cake and a superior baked product.

Additionally, processes for milling sucrose to make smaller, finer particles, i.e., powdered sugar, are well known. It has been found that co-milling of sucrose with starch, a complex sugar, results in a superior powdered product. The starch acts as an anti-caking agent and causes the final powdered product to be more uniform in consistency, whereby the particulate size distribution is relatively constant, and the powdered product flows easily and smoothly without clumping.

In many conventional processes for forming co-milled polyols, the components which are co-milled are generally compatible with one another and are suitable for human consumption. However, polyols such as sucrose are often used as reactants and/or precursors for other useful products, one example of which is polyol fatty acid polyesters. Polyol fatty acid polyesters are useful as low calorie fats in various food products. Polyol and fatty acid lower alkyl esters are reacted in the presence of catalysts, to produce polyol fatty acid polyesters. However, polyols are typically hydrophilic while fatty acid lower alkyl esters are typically hydrophobic, whereby it may often prove difficult to form mixtures of the polyol and fatty acid lower alkyl ester in a solvent free transesterfication reaction. In order to achieve the desired transesterfication of the polyol, it is often necessary to bring the polyol and the fatty acid ester into the same phase. Alkali metal fatty acid soaps are conventional emulsifiers for transesterfication reactions of polyols using fatty acid lower alkyl esters, although other emulsifiers have been used to help solubilize the polyol in the lower alkyl esters.

There is a continuing necessity to improve processes for the manufacture of polyol fatty acid polyesters, including, inter alia, to provide a superior polyol feed stream for use in the transesterfication reaction of the polyol.

SUMMARY OF THE INVENTION

Accordingly, it is an object of the present invention to provide an improved process for manufacturing polyol fatty acid polyesters, and, more particularly, it is an object of the present invention to provide an improved polyol feed stream for use, inter alia, in the transesterfication of polyol to produce polyol fatty acid polyesters. It is a related object of the present invention to provide a co-milled mixture of a polyol and one or more of a catalyst, an emulsifier or other reaction component employed in the manufacture of polyol fatty acid polyesters.

These and additional objects are provided by the present invention. Specifically, the invention, in one embodiment, is directed to a co-milled mixture of a solid polyol and one or more of a catalyst, an emulsifier or other reaction component employed in the manufacture of polyol fatty acid polyesters. Preferably, the co-milled product comprises finely ground particles of the polyol and finely ground particles of another reaction component, and finely ground particles of an admixture of polyol and another component. In a preferred embodiment, the polyols are selected from the group consisting of monosaccharides, disaccharides, sugar alcohols, polyethyoxylated glycerols, polyglycerols, sugar ethers and mixtures thereof. In another preferred embodiment, an alkali metal fatty acid soap is selected from the group consisting of alkali metal salts of saturated and unsaturated fatty acids having from about 8 to about 18 carbon atoms.

In another embodiment, the invention is directed to a process for co-milling a polyol and one or more of a catalyst, an emulsifier or other reaction component employed in the manufacture of polyol fatty acid polyesters, wherein a crushing or grinding mill is used for co-milling. The crushing or grinding mill can be a gas swept hammer mill, a jet mill, a multi-impact stud mill, a bead mill, or the like. In an especially preferred process, a gas swept hammer mill having a rotating disc is used. In yet a further embodiment of the present invention, a co-milled mixture of a polyol and an alkali metal fatty acid soap is used to form polyol fatty acid polyesters.

Co-milled mixtures of polyol and one or more of a catalyst, an emulsifier or other reaction component of the present invention provide an advantage over milled polyol in that the co-milled mixtures are free-flowing and they do not readily agglomerate. Co-milled mixtures of the present invention provide the further advantage of providing a single feed source for a transesterfication reaction of polyol, wherein the single feed source combines two or more essential ingredients, e.g., the polyol, the soap, emulsifiers or other components. It is a further advantage of the present invention to provide a polyol which has been milled so as to provide finely ground particles of the polyol, wherein "finely ground" is meant to include average particle size of below about 100μ, preferably below about 50μ, and most preferably below about 10μ. The small average particle size provides increased surface area of the polyol which increases the rate of mass transfer in a transesterfication reaction. It is yet another advantage of the present invention to provide a superior method of milling polyol by the incorporation of a milling aid which is also a reaction component in the reaction of a polyol to form a polyol fatty acid polyester.

These and additional objects and advantages will be more apparent in view of the following detailed description.

DETAILED DESCRIPTION

As used herein, the term "polyol" is intended to include any aliphatic or aromatic compound containing at least two free hydroxyl groups. It is understood that liquid polyols are not suitable for co-milling, and thus, only polyols in the solid or semi-solid state are considered appropriated for the co-milled mixtures described herein. For example, suitable polyols may be selected from the following classes: saturated and unsaturated, straight and branched chain, linear aliphatics; saturated and unsaturated, cyclic aliphatics including heterocyclic aliphatics; or mononuclear and polynuclear aromatics including heterocyclic aromatics.

Preferred polyols for use in producing the co-milled mixture described herein include monosaccharides, disaccharides, sugar alcohols and mixtures thereof. Accordingly, monosaccharides suitable for use herein include, for example: glucose, mannose, galactose, arabinose, xylose, ribose, abiose, rhamnose, psicose, fructose, sorbose, tagintose, ribulose, xylulose, and erythrulose. Disaccharides suitable for use herein include, but are not limited to, maltose, cellobiose, lactose, and sucrose. The sugar alcohols most widely distributed in nature and suitable for use are sorbitol, mannitol, and galactitol. Especially preferred polyols for use herein include xylitol, sorbitol, and sucrose. Polyethyoxylated glycerols, polyglycerols, and sugar ethers can also be used herein.

Polysaccharides, for example carbohydrates and starches, are polyols and are also suitable for use in manufacturing the co-milled mixture described herein. However, because an especially preferred use for the co-milled mixture of the present invention is as a feed stock for a transesterfication reaction of the polyol to produce a polyol fatty acid polyester, the preferred polyols listed above, i.e., monosaccharides, disaccharides, and sugar alcohols, are preferred polyols for transesterfication to produce polyol fatty acid polyesters, although they are not necessarily superior to polysaccharides for the purpose of producing a co-milled mixture of polyol and other reaction components according to the invention.

As used herein, the term "other reaction component" is intended to include any solid component suitable for use in a reaction of a polyol to produce a polyol fatty acid polyester. As will be discussed in greater detail below, the solid polyol and other solid reaction components can be co-milled in the presence of a fluid, however, the co-milling must necessarily occur between solid components. Suitable reaction components can include, but are not limited to, emulsifiers, catalysts and mixtures thereof Preferred emulsifiers for the reaction of a polyol to form a polyol fatty acid polyester include alkali metal fatty acid soaps.

As used herein, the term "alkali metal fatty acid soap" is intended to include the alkali metal salts of saturated and unsaturated fatty acids having from about eight to about twenty four carbon atoms. To make edible polyol polyesters, the alkali metal should be edible, i.e., sodium or potassium. Accordingly, suitable alkali metal fatty acid soaps include, for example, the lithium, sodium, potassium, rubidium, and cesium salts of fatty acids such as capric, lauric, myristic, palmitic, linoleic, oleic, and stearic acids, as well as mixtures thereof. Mixtures of fatty acids derived from soybean oil, sunflower oil, safflower oil, canola oil, high erucic acid rapseed oil and corn oil are preferred for use herein. These fatty acids can be hydrogenated. Especially, preferred alkali metal fatty acid soaps include, for example, the potassium soap made from polmetic and stearic acids.

In addition to alkali metal soaps, other solid emulsifiers such as sucrose fatty acid mono, di and triesters can be used. Solid mono and diglycerides can also be used, although they are less preferred. The polyol can also be co-milled with the transesterfication catalyst, e.g., potassium methoxide or potassium carbonate. The co-milling of polyols with alkali metal soaps has been used to exemplify the present invention but should not be read as limiting, as discussed above, other reaction components, e.g. emulsifiers and catalysts, are also suitable for use in the co-milling processes described herein.

Co-milling of polyols and other reaction components can be accomplished through a variety of known milling processes, e.g., crushing mills, grinding mills or combinations thereof. For an in-depth discussion of particulate size reduction in general, and crushing and grinding mills in particular, see *Perry's Chemical Engineers Handbook;* Sixth Edition, pages 8–10 through 8–60, McGraw and Hill, New York, 1984, the disclosure of which is incorporated herein by reference. Jaw crushers, roll crushers, impact breakers, tumbling mills, ball or bead mills, hammer mills, jet mills, or combinations of the above are all appropriate mechanical methods for producing the co-milled mixtures described herein.

The mechanical mills listed above can generally be classified into four groups. The first group includes mills which employ crushing and shearing forces between two hard surfaces. Examples are roll mills and ball mills. The second group includes mills which employ a screen, grid, or grating through which the material to be ground is forced. Most hammer mills are exemplary of this type of mill. The third group includes mills which employ a suspension of the material to be ground in a liquid such as water or oil. Examples are "attritors" and some types of roller mills. The fourth group includes impact mills wherein the material to be ground is reduced in size by striking a hard surface which can be a rotating member of the device, a stationary member of the device, another particle of the material being treated, and/or mixtures of these three types of impact surfaces. Impact mills can further be classified into sub-types as follows: (a) "one pass" impact mills where there is no internal provision for recirculating oversized material or grinding the material into several internal stages and where there is little or no co-action between the particles being treated; and (b) multi-pass impact mills which employ an internal particle size classifier to return oversized material for further grinding, or which subject material to repeated grinding actions in several internal stages. These multi-impact mills involve a substantial co-action between particles of the material being treated. The second group of mills described above, employing a screen, grid or grating, and the multi-pass impact mills are preferred for co-milling polyols and fatty acid soaps as described herein.

More specifically, a gas swept hammer mill is especially preferred for co-milling polyols and fatty acid soaps. A typical gas swept hammer mill has a rotating disk situated horizontally wherein particles to be co-milled are introduced above the rotating disk and the gas is introduced from the sides. The gas is typically air or nitrogen gas, although other gasses may be employed, and is typically introduced at flow rates of from about 800 CFM, to about 1,600 CFM. The exact flow rate will depend on the desired particle size. The dry air or the dry nitrogen gas is typically fed into the hammer mill at a temperature of not greater than about 60° F. (16° C.). As can be appreciated, heat is generated during the crushing and/or grinding operations and some of that heat is transferred to the air or the nitrogen gas which generally exits the mill at a temperature not less than about 100° F. (38° C.).

As is discussed in greater detail below, the moisture content of the co-milled mixture should be kept to a minimum to avoid caking/agglomerating of the co-milled particles. A preferred moisture content for co-milled mixtures of the present invention is less than about 2% by weight. Accordingly, the air or nitrogen is typically dried to a moisture content of less than about 1% by weight prior to use. The preferred polyols of the present invention are generally hydrophilic, i.e., moisture introduced into the milling process will generally be absorbed by the co-milled mixture, thus, promoting caking and undesirable flow characteristics of the resultant particulate product.

As will be appreciated, the rotation speed of the horizontal disk is generally proportional to the disk diameter. Particles in a gas swept hammer mill are typically crushed near the tip of the rotating disk, thus, it is the "tip speed" of the rotating disk, i.e., the speed of the disk at its outer circumference, which is crucial for the control of the resultant particle size of the co-milled mixture. Thus, the revolutions per minute of a 20" (50 cm) diameter rotating disk would be significantly higher than the rotation speed of a 40" diameter rotating disk to maintain a constant tip speed. Tip speed will vary between different equipment, different polyols, the nature and amount of the other reaction components, and their proportional relationship, and the desired particulate size and composition. However, as an example, using a 20" (50 cm) rotating horizontal disk, speeds of 5,000 to 6,250 revolutions per minute were used to achieve a suitable particle size as disclosed herein. Likewise, using a 38" (95 cm) diameter rotating disk, the speed was reduced to 1,500 to 2,500 revolutions per minute while maintaining the same particulate size distribution.

Particulate size distribution is further controlled by the rate of introduction of gas to the hammer mill. Gas is fed into the mill from the sides, drawn through the rotating disk, and up and out of the mill. As gas is pulled through the mill, the smaller, finer particles are carried out in the gas stream. Typically, the gas stream is then directed towards a filtering system, e.g., a bag house, where the particulates are separated from the gas stream and the particulate-free gas is either expelled or recycled to the mill process. As will be apparent, the greater the flow of gas through the mill, the larger the particles that will be carried out of the mill in the gas and into the filter system. Thus, by increasing the flow of gas through the system and maintaining all other process variables constant, the average diameter of particles collected will also be increased.

Wet milling of polyols and other reaction components is generally more complicated in that an additional component, i.e., a liquid carrier, is required for the milling process. However, wet milling is equally functional for producing the desired co-milled product of polyol and other reaction components. When wet milling is employed, an appropriate liquid carrier must be chosen. Many polyols, e.g., sucrose, fructose, and sorbitol, dissolve readily in water which makes water an inappropriate milling aid. Especially preferred liquid milling aids for use with the polyols and fatty acid soaps disclosed herein are fatty acid lower alkyl esters or lower alkyl fatty acid esters of the polyol. As will be apparent, in the transesterfication of polyols to form a polyol fatty acid polyester, fatty acid lower alkyl esters are a preferred reactant, along with the polyol, fatty acid soap, and a catalyst. Thus, using a fatty acid lower alkyl ester as a milling aid provides the additional benefit of the incorporation of an additional reactant, as opposed to an inert, in the co-milled mixture. The moisture level of the fatty acid lower alkyl ester and the other reaction components should be less than about 1.0%.

It has been found that co-milling of polyol and fatty acid soaps results in an unexpected attendant benefit of lower energy consumption as compared with milling a polyol alone. While not wanting to be restricted to any particular theory, it is believed that the soap acts as a milling aid, i.e., the polyol is more easily milled in the presence of a fatty acid soap. It has been found that the amperage required to mill a polyol/soap mixture is significantly less than when milling the polyol alone using the same mill. Furthermore, soap has been observed to aid in the creation of smaller particles of the co-milled mixture. More particularly, and as is demonstrated by the tabulated test data reproduced below, with all other processing parameters held constant, milling polyol alone results in the formation of larger particles as compared with milling the same polyol in the presence of a soap.

Additionally, the co-milling of a polyol in the presence of a fatty acid soap results in a mixture with superior flow characteristics when compared to milled polyol which does not include soap, i.e., the soap has an anti-caking effect. While not wanting to be restricted to any one theory, it is believed that caking of the polyol is caused by the agglomeration of particles through the formation of "liquid bridges", i.e., water incorporated within the polyol tends to form bridges between individual polyol particles. As multiple bridges are formed, clumps of polyol particles are formed which generally have an adverse effect on the flow characteristics of the milled polyol. However, it is believed that the formation of liquid bridges may be deterred when the polyol is co-milled with soap because the polyol particles become at least partially coated with the soap. As can be appreciated, soap is hydrophobic and acts to deter the attachment of water which forms the "liquid bridges."

Anti-caking agents such as starch and other polysaccharides have been co-milled with polyols, e.g., sucrose, for the production of a free flowing, non-caking, polyol product. However, anti-caking agents of the past were typically inert and were added in very small amounts because the anti-caking agent was not considered part of the product For purposes of producing a polyol fatty acid polyester, both the polyol and alkali metal fatty acid soap are required reactants. Thus, both constituents of the co-milled mixture disclosed herein are desired feed streams to the transesterfication reaction of the polyol.

Co-milling the polyol and soap has the additional benefit of mixing two active ingredients, as opposed to an active ingredient and an inert substance which does not participate in the reaction process and which must later be removed. That is, co-milling a polyol with an anti-making agent, such as starch, generally requires the removal of the starch or its reaction or degradation products from the final product stream. Moreover, the final product stream will generally be more pure if the number and amount of compounds which do not actively participate in the reaction are reduced or eliminated from the initial reaction mixture, because most separation processes will leave at least trace amounts of the impurification in the product stream. Ultimately, for purposes of the transesterfication reaction, two feed streams, e.g., the polyol and the alkali metal fatty acid soap, can be reduced to one homogeneous feed stream, i.e., the co-milled mixture of the present invention. This results in significant processing and economic advantages in the production of polyol fatty acid polyesters.

Generally, the transesterfication of a polyol proceeds slower than would be predicted through thermodynamic or reaction kinetic estimations. While not wanting to be bound by this theory, it is believed that the reaction is mass transfer limited, i.e., the speed of the reaction occurs only as fast as the molecules of polyol and fatty acid lower alkyl ester can be brought together physically in order to react chemically. As will be apparent, the alkali metal fatty acid soap acts as an emulsifier to bring the polyol and fatty acid lower alkyl ester into the same phase so that they can make physical contact and thus, chemically react. The introduction of the polyol in intimate contact with the phase transfer agent or emulsifier, promotes the contact of the fatty acid lower alkyl ester with the polyol, hence, promoting the transesterfication reaction.

The reduced particle size of the co-milled polyol significantly increases the surface area of polyol available for reaction with the fatty acid lower alkyl ester. The smaller the size of the reactant particles, the greater the reaction surface area available, hence it is easier for particles from different phases, i.e., polyol and fatty acid lower alkyl ester, to contact one another and to chemically react. Thus, the reduction in size of the co-milled particles produces a significant processing advantage.

An average particulate size for the co-milled mixture of the present invention is preferably not greater than about 100μ, more preferably not greater than about 50μ, and most preferably not greater than about 10μ. Particle size can be measured by a variety of commercially available means. Vibrating or vacuum sieves are common particle size classifiers. It is preferred that after co-milling greater than about 98% of the polyol and fatty acid soap particles pass through a 325 mesh, which has an effective opening of about 44μ. Laser diffraction measurements can also be performed with commercially available equipment, for example the Malvern Particle Size Analyzer. Laser diffraction involves fluidizing particles in a gas stream and then passing the particles through a laser beam. Through the use of a microprocessor, the laser can classify the particles and report the results in terms of particle size distribution, and average particle size.

At the completion of the transesterfication reaction of the polyol, the fatty acid soap is typically removed from the polyol fatty acid polyester product stream. As is described above, the presence of the fatty acid soap is important to the transesterfication reaction because the soap acts as an emulsifier. However, soap is generally not desired in the final product stream. Thus, it is desirable to keep the amount of soap in the co-milled mixture to a minimum while retaining the emulsifier benefits. It has been found that co-milling polyol and fatty acid soap in weight ratios of about 2:1 (polyol:fatty acid soap) is acceptable, with lower amounts of soap being preferred, and a polyol:soap weight ratio of about 4:1 is more preferred. The desired results described herein can be achieved by co-milling polyol and soap in weight ratios of polyol:soap of about 100:1 about 2:1 and preferably from about 50:1 to about 4:1. As will be apparent, while higher concentrations of soap are physically possible, and while the co-milled mixture can still be suitable for use in a transesterfication reaction, is not desired. High amounts of soap result in increased production costs, i.e., when the polyol fatty acid polyester product stream is purified to remove it.

The following example is provided to demonstrate specific embodiments of the present invention.

EXAMPLE

To exemplify the products and processes described herein, sucrose and potassium stearate particles are dry co-milled and the resulting particle diameters are measured after co-milling. The six tests reported below are all run at essentially the same conditions and in the same mill. Median size is defined as the particle diameter where 50% by volume of the particles have a greater diameter and 50% by volume have a smaller diameter. The particle diameters are measured with a Malvern particle size analyzer, available from Malvern instruments, the operation of which is discussed in greater detail above.

The initial concentration of sucrose and stearate is varied from 100% sucrose and 0% stearate to 60% sucrose and 40% stearate. The initial average particle size of the potassium stearate is not greater than about 100μ. Preferably the soap is supplied as a fine powdery substance with an average particle size of not greater than about 20μ. The sucrose is initially granular with from about 50% to about 100% by volume of the particles having a diameter of greater than about 250μ, subject to the additional restrictions that no more than 10% by volume of the particles having a diameter of less than about 150μ and no more than about 4% by volume of the particles having a diameter of greater than about 840μ.

As can be seen in the table below, the addition of as little as 0.3% stearate to the sucrose prior to milling results in a 25% reduction in final particle size, i.e., from 17.77μ to 13.24μ. The average median particle size for the last three entries, i.e., 85%, 81% and 60% sucrose, is 8.0μ which represents a 55% reduction in particle size with the addition of 15% or more stearate. As should be apparent, varying the milling conditions, e.g., air flow rate, particle flow rate or moisture content, or varying the physical parameters of the mill, e.g., type or size of the mill, will generally affect the median particle size for a given mixture of sucrose to stearate. Thus, the particle sizes tabulated below are not meant to be limiting but rather are intended to illustrate the significant reduction in particle size which is obtained as stearate is added to sucrose prior to the milling process.

| SUCROSE (% by weight) | STEARATE (% by weight) | MEDIAN SIZE |
| --- | --- | --- |
| 100 | 0 | 17.77 μ |
| 99.7 | 0.3 | 13.24 μ |
| 95 | 5 | 10.01 μ |
| 85 | 15 | 7.77 μ |
| 81 | 19 | 8.3 μ |
| 60 | 40 | 8.03 μ |

Having shown and described the preferred embodiments of the present invention, further adaptation of the co-milled mixtures of polyol and other reaction components for the manufacture of polyol fatty acid polyesters and methods of making the same can be accomplished by appropriate modifications by one of ordinary skill in the art without departing from the scope of the present invention. A number of alternatives and modifications have been described herein and others will be apparent to those skilled in the art. For example, specific methods of co-milling polyols and soaps have been described, although other manufacturing processes can be used to produce the desired co-milled mixture. Likewise, numerous polyols and other reaction components have been disclosed for the co-milled mixture as preferred embodiments of the present invention, yet the constituents can be varied to produce other preferred embodiments of the co-milled mixtures of the present invention as desired. Accordingly, the scope of the present invention should be considered in terms of the following claims and is understood not be limited to the details of the compositions and methods shown and described in the specification.

I claim:

1. A process for making a mixture of a solid polyol and at least one additional solid reaction component, wherein the additional solid reaction component comprises a component employed in the manufacture of polyol fatty acid polyesters, the process comprising co-milling the polyol with the at least one additional solid reaction component to form a co-milled mixture.

2. The process according to claim 1, wherein the at least one additional reaction component is selected from the group consisting of emulsifiers, catalysts, and mixtures thereof.

3. The process according to claim 1, wherein the at least one additional reaction component is an emulsifier comprising an alkali metal fatty acid soap.

4. The process according to claim 1, wherein the co-milled mixture comprises finely ground particles of the polyol, finely ground particles of an admixture of the polyol and the at least one additional reaction component, and finely ground particles of the at least one additional reaction component.

5. The process according to claim 4, wherein the finely ground particles have an average particle diameter of not greater than about 100 microns.

6. The process according to claim 1, wherein the moisture content of the co-milled mixture is not greater than about 2% by weight.

7. The process according to claim 1, wherein the polyol is selected from the group consisting of monosaccharides, disaccharides, sugar alcohols, polyglycerols, polyethoxolated glycerols, sugar ethers and mixtures thereof.

8. The process according to claim 1, wherein the polyol is selected from the group consisting of sucrose, xylitol, sorbitol and mixtures thereof.

9. The process according to claim 3, wherein the fatty acid soap is selected from the group consisting of alkali metal salts of saturated and unsaturated fatty acids having from about eight to about twenty four carbon atoms.

10. The process according to claim 3, wherein the fatty acid soap is selected from the group consisting of lithium, sodium, potassium, rubidium and cesium salts of capric, lauric, myristic, palmitic, linoleic, oleic and stearic acids, and mixtures thereof.

11. The process according to claim 1, wherein a crushing or grinding mill is used to make the co-milled mixture, and the crushing or grinding mill is a gas swept hammer mill, a jet mill, a multi-impact stud mill, or a bead mill.

12. The process according to claim 11, wherein the crushing or grinding mill is a gas swept hammer mill.

13. The process according to claim 12, wherein the dry air or the dry nitrogen gas is fed into the hammer mill at a temperature of not greater than about 60° F. (16° C.) and the air or the nitrogen gas exits the hammer mill at a temperature not less than about 100° F. (38° C.).

14. The process according to claim 1, wherein the polyol and the at least one additional reaction component are fed into the crushing or grinding mill at a weight ratio of polyol to at least one additional reaction component of from about 2:1 to about 100:1.

15. The process according to claim 1, wherein polyol and at least one additional reaction component are wet milled in the presence of a fatty acid lower alkyl ester.

16. A particulate composition comprising a co-milled mixture of a solid polyol and at least one additional solid reaction component, wherein the additional solid reaction component comprises a component employed in the manufacture of polyol fatty acid polyester.

17. The particulate composition according to claim 16, wherein the at least one additional reaction component is selected from the group consisting of emulsifiers, catalysts and mixtures thereof.

18. The particulate composition according to claim 17, wherein the at least one additional reaction component is an emulsifier comprising an alkali metal fatty acid soap.

19. The particulate composition according to claim 16, wherein the co-milled mixture comprises finely ground particles of the polyol, finely ground particles of an admixture of the polyol and at least one additional reaction component, and finely ground particles of the at least one additional reaction component.

20. The particulate composition according to claim 19, wherein the finely ground particles have an average particle diameter of not greater than about 100 microns.

21. The particulate composition according to claim 16, wherein the moisture content of the co-milled mixture is not greater than about 2% by weight or less.

22. The particulate composition according to claim 16, wherein the polyol is selected from the group consisting of monosaccharides, disaccharides, sugar alcohols, polyethoxylated glycerols, polyglycerols, sugar ethers and mixtures thereof.

23. The particulate composition according to claim 16, wherein the polyol is selected from the group consisting of sucrose, xylitol, sorbitol and mixtures thereof.

24. The particulate composition according to claim 18, wherein the fatty acid soap is selected from the group consisting of alkali metal salts of saturated and unsaturated fatty acids having from about eight to about twenty four carbon atoms.

25. The particulate composition according to claim 24, wherein the fatty acid soap is selected from the group consisting of lithium, sodium, potassium, rubidium and cesium salts of capric, lauric, myristic, palmitic, linoleic, oleic and stearic acids, and mixtures thereof.

26. The particulate composition according to claim 16, wherein a crushing or grinding mill is used to make the co-milled mixture, and the crushing or grinding mill is a gas swept hammer mill, a jet mill, a multi-impact stud mill, or a bead mill.

27. The particulate composition according to claim 26, wherein the crushing or grinding mill is a gas swept hammer mill.

28. The particulate composition according to claim 27, wherein the dry air or the dry nitrogen gas is fed into the hammer mill at a temperature of not greater than about 60° F. (16° C.) and the air or the nitrogen gas exits the hammer mill at a temperature of not less than about 100° F. (38° C.).

29. The particulate composition according to claim 16, wherein the polyol and the at least one additional reaction component are fed into the crushing or grinding mill at a weight ratio of polyol to at least one additional reaction component of from about 2:1 to about 100:1.

30. The particulate composition according to claim 16, wherein the solid polyol and the at least one additional reaction component are wet milled in the presence of a fatty acid lower alkyl ester.

31. A process for making a polyol fatty acid polyester comprising:
co-milling a solid polyol and at least one additional solid reaction component for the manufacture of polyol fatty acid polyester to form a co-milled mixture; and
combining the co-milled mixture with a fatty acid lower alkyl ester in the presence of a catalyst to react the polyol and the fatty acid lower alkyl ester to produce the polyol fatty acid polyester.

32. A process for making a polyol fatty acid polyester comprising:
co-milling a solid polyol and at least one additional solid reaction component selected from the group consisting of emulsifiers, catalysts, and mixtures thereof to form a co-milled mixture; and combining the co-milled mixture with a fatty acid lower alkyl ester in the presence of a catalyst to react the polyol and the fatty acid lower alkyl ester to produce the polyol fatty acid polyester.

33. The process according to claim 32, wherein the at least one additional reaction component is an emulsifier comprising an alkali metal fatty acid soap.

34. The process according to claim 31, wherein the co-milled mixture comprises finely ground particles of the polyol, finely ground particles of an admixture of the polyol and the at least one additional reaction component, and finely ground particles of the at least one additional reaction component.

35. The process according to claim 34, wherein the finely ground particles have an average particle diameter of not greater than about 100 microns.

36. The process according to claim 31, wherein the moisture content of the co-milled mixture is not greater than about 2% by weight.

37. The process according to claim 31, wherein the polyol is selected from the group consisting of monosaccharides, disaccharides, sugar alcohols, polyethyoxylated glycerols, polyglycerols, sugar ethers and mixtures thereof.

38. The process according to claim 31, wherein the polyol is selected from the group consisting of sucrose, xylitol, sorbitol and mixtures thereof.

39. The process according to claim 33, wherein the fatty acid soap is selected from the group consisting of alkali metal salts of saturated and unsaturated fatty acids having from about eight to about twenty four carbon atoms.

40. The process according to claim 39, wherein the fatty acid soap is selected from the group consisting of lithium, sodium, potassium, rubidium and cesium salts of capric, lauric, myristic, palmitic, linoleic, oleic and stearic acids, and mixtures thereof.

41. The process according to claim 31, wherein a crushing or grinding mill is used to make the co-milled mixture, and the crushing or grinding mill is a gas swept hammer mill, a jet mill, a multi-impact stud mill, or a bead mill.

42. The process according to claim 41, wherein the crushing or grinding mill is a gas swept hammer mill.

43. The process according to claim 42, wherein the dry air or the dry nitrogen gas is fed into the hammer mill at a temperature of not greater than about 60° F. (16° C.) and the air or the nitrogen gas exits the hammer mill at a temperature of not less than about 100° F. (38° C.).

44. The process according to claim 31, wherein the polyol and the at least one additional reaction component are fed into the crushing or grinding mill at a weight ratio of polyol to at least one additional reaction component of from about 2:1 to about 100:1.

45. The process according to claim 31, wherein the polyol and the at least one additional reaction component are wet milled in the presence of a fatty acid ester.

46. The process according to claim 32, wherein the polyol is selected from the group consisting of monosaccharides, disaccharides, sugar alcohols, polyethoxylated glycerols, polyglycerols, sugar ethers and mixtures thereof.

47. A particulate composition comprising a co-milled mixture of finely ground particles of a polyol, finely ground particles of an admixture of the polyol and at least one additional reaction component for the manufacture of polyol fatty acid polyester, and finely ground particles of the at least one additional reaction component; wherein the at least one additional reaction component is selected from the group consisting of emulsifiers, catalysts and mixtures thereof.

48. The particulate composition according to claim 47, wherein the finely ground particles have an average particle diameter of not greater than about 100 microns.

49. The particulate composition according to claim 47, wherein the moisture content of the co-milled mixture is not greater than about 2% by weight or less.

* * * * *

UNITED STATES PATENT AND TRADEMARK OFFICE
CERTIFICATE OF CORRECTION

PATENT NO. : 5,914,320
DATED : June 22, 1999
INVENTOR(S) : Steven R. Alexander

It is certified that error appears in the above-indentified patent and that said Letters Patent is hereby corrected as shown below:

Claim 21, line 15, delete "or less".

Claim 49, line 36, delete "or less".

Signed and Sealed this

Twenty-third Day of November, 1999

Attest:

Attesting Officer

Q. TODD DICKINSON

Acting Commissioner of Patents and Trademarks